(12) United States Patent
Suzuki et al.

(10) Patent No.: US 7,201,512 B2
(45) Date of Patent: Apr. 10, 2007

(54) KNEADER FOR TOOTH RESTORATION MATERIAL

(75) Inventors: Yoshimasa Suzuki, Tokyo (JP); Masaaki Kaneko, Tokyo (JP)

(73) Assignee: GC Corporation, Tokyo (JP)

( * ) Notice: Subject to any disclaimer, the term of this patent is extended or adjusted under 35 U.S.C. 154(b) by 87 days.

(21) Appl. No.: 11/149,210

(22) Filed: Jun. 10, 2005

(65) Prior Publication Data

US 2005/0282104 A1 Dec. 22, 2005

(30) Foreign Application Priority Data

Jun. 22, 2004 (JP) ............................. 2004-183555

(51) Int. Cl.
*B01F 9/22* (2006.01)

(52) U.S. Cl. .................................... 366/217

(58) Field of Classification Search ................ 366/139, 366/209–219, 602; 433/49, 90, 91; 494/19
See application file for complete search history.

(56) References Cited

U.S. PATENT DOCUMENTS 4,586,292 A * 5/1986 Carroll et al. .............. 366/219
5,167,448 A 12/1992 Herold et al.
6,733,170 B2 * 5/2004 Mukasa et al. ............. 366/139

FOREIGN PATENT DOCUMENTS

| EP | 1 316 296 A1 | | 6/2003 |
| JP | 3-193127 | * | 8/1991 |
| JP | 2002-35563 | | 2/2002 |
| JP | 3468367 | | 9/2003 |
| JP | 2004-243158 | * | 9/2004 |

* cited by examiner

*Primary Examiner*—Charles E. Cooley
(74) *Attorney, Agent, or Firm*—Oblon, Spivak, McClelland, Maier & Neustadt, P.C.

(57) ABSTRACT

To mix powder and liquid components evenly, a kneader comprises a rotating plate rotated around a driving axis; a bearing for a capsule housing body mounted near a circumference part of the plate, wherein an axis supported with the bearing is rotatable only in a reverse direction to a rotating direction of the plate; a capsule housing body fixed at a capsule housing body supporting axis in parallel to the driving axis and supported with the bearing; a balance weight fixed at a predetermined position of the plate approximately opposite to the body beyond the driving axis; and a mechanism for circularly moving an axis for keeping the direction of the body in the same direction as the rotating direction of the plate along a circle having the same diameter as but the different center from those of the body supporting axis.

5 Claims, 4 Drawing Sheets

KNEADER FOR TOOTH RESTORATION MATERIAL

BACKGROUND OF THE INVENTION

1. Field of the Invention

The present invention relates to a kneader for a tooth restoration material, which circularly moves a capsule for a tooth restoration material while keeping its longitudinal direction in a fixed direction, in order to mix and knead a powder component and a liquid component of the tooth restoration material in a mixing compartment of the capsule for the tooth restoration material.

2. Description of the Conventional Art

In a dental treatment, the tooth restoration material is used for application, such as a filling, a luting, a lining or the like to restore the tooth by mixing and kneading the powder component and the liquid component immediately before using thereof. Thus, the capsule for the tooth restoration material, in which the fixed amounts of the powder component and the liquid component are weighed beforehand and housed isolatedly in the mixing compartment, is widely used in order to easily mix and knead those without soiling hands.

In general, the capsule for the tooth restoration material is used by breaking a partition or the like immediately before using thereof, and mixing and kneading two components, i.e., the powder component and the liquid component for the tooth restoration material. At this time, if the two components are not fully mixed and kneaded, the tooth restoration material becomes fragile, and if these components are mixed and kneaded excessively, the tooth restoration material is inconvenient to use since it is hardened immediately. Thus, the kneader for the tooth restoration material is used for exactly mixing and kneading. However, since the conventional kneader for the tooth restoration material only reciprocates the capsule for the tooth restoration material in one direction such as a longitudinal direction, there is a problem that the two components are not mixed and kneaded evenly since they receive the force only in the direction of the reciprocating movement of the capsule.

For solving the above problem, a kneader for a capsule for the tooth restoration material as follows is used in order to evenly mix and knead the two components for the tooth restoration material while they receive the force in various directions without generating bubbles in the mixed and kneaded material (for example, refer to Japanese Patent No. 3468367). The kneader comprises a capsule retaining chamber rotating means, which circularly moves the capsule retaining chamber itself for retaining the capsule for the tooth restoration material with its longitudinal direction being kept in a fixed direction, a driving means for driving the capsule retaining chamber rotating means, and a vacuum generator connected with the capsule retaining chamber. In the kneader for the capsule for the tooth restoration material, in order to circularly move a rotating table, where the capsule retaining chamber is rotatably supported around a fixed axis, the fixed axis and the capsule retaining chamber are connected with a timing belt so as to rotate the capsule retaining chamber in a reverse direction to the rotating direction of a pulley at the same angle as the rotating angle of the pulley fixed at the rotating table. Thus, the capsule retaining chamber on the rotating table circularly moves in the state of being kept in the fixed direction. Then, the two components for the tooth restoration material in the capsule for the tooth restoration material can be evenly mixed and kneaded while they receives the force in various directions.

However, in this kneader for the capsule for the tooth restoration material, the timing belt is used for rotating the capsule retaining chamber, and this timing belt is different from a general timing belt which is rotated and moved at high speed between the pulleys by the rotation of the pulley being compulsorily rotated. That is, when the rotating table is rotated around the fixed axis, this timing belt is rotated and moved at low speed around the fixed axis only at the angle as much as the rotating table is rotated, that is, the capsule retaining chamber is rotated with respect to the fixed axis. Thus, there is a problem that the accuracy of the timing belt cannot be kept when the timing belt is abraded or loosened even a little by the deterioration with the passage of time.

That is, in the conventional kneader for the capsule for the tooth restoration material, since the timing belt must be exactly rotated and moved around the fixed axis only at the angle as much as the capsule retaining chamber is rotated with respect to the fixed axis, the engaging accuracy of teeth of the pulley and the timing belt must be remarkably high. Further, since the timing belt formed with a rubber or the like is in the exposed state, a problem of the timing belt being quickly deteriorted or deformed is generated when chemicals or the like adhere. Thus, this conventional kneader is not preferably used in the dental treatment fields.

SUMMARY OF THE INVENTION

In view of the above-mentioned problems, the primary objective of the present invention is to provide the kneader for the tooth restoration material, which can exactly synchronize the circular movement with the rotating movement without using the timing belt or the like, has high durability, and is hardly deteriorated even when the chemicals or the like adhere.

The earnest work was carried out in order to solve the above-mentioned problems and, as a result of this, the followings were found out to complete the invention. When the kneader for the tooth restoration material comprises a rotating plate, a bearing for a capsule housing body, a capsule housing body, a balance weight, and a mechanism described below respectively, the capsule housing body housing the capsule for the tooth restoration material can be circularly moved in the state of always being kept in the fixed direction. The rotating plate is rotated by a driving means centering on the driving axis. The bearing for the capsule housing body is mounted near a circumference part of the rotating plate, wherein the axis supported with this bearing is only rotatable in a reverse direction to a rotating direction of the rotating plate. The capsule housing body is fixed at a capsule housing body supporting axis, which is parallel to the driving axis of the driving means and supported with the bearing for the capsule housing body. The balance weight is fixed at a predetermined position of the rotating plate, where this position is approximately opposite to the capsule housing body centering the driving axis of the driving means. The mechanism is for circularly moving an axis for keeping the direction of the capsule housing body (hereinafter said to as the direction keeping axis) in the same direction as the rotational direction of the rotating plate, along a circle having the same diameter as but the different center from those of the circular movement of the capsule housing body supporting axis, and the direction keeping axis is parallel to the driving axis of the driving means, and substantially fixed with the capsule housing body. When the kneader for the tooth restoration material has the above constitution, the capsule housing body supporting axis and the direction keeping axis can be circularly moved in the same direction along circles having the same diameters but the different centers respectively, so as to always make a line connecting between center lines of the capsule housing body supporting axis and the direction keeping axis in the same direction. Therefore, the capsule housing body housing the capsule for the tooth restoration material can be circularly moved in the state of always being the fixed direction.

That is, the present invention relates to the kneader for the tooth restoration material, which circularly moves the capsule housing body housing and keeping the capsule for the tooth restoration material, with its longitudinal direction being kept in the fixed direction, in order to mix and knead the powder component and the liquid component of the tooth restoration material in the mixing compartment of the capsule for the tooth restoration material. The kneader for the tooth restoration material comprise the rotating plate, the bearing for the capsule housing body, the capsule housing body, the balance weight and the mechanism described below respectively. The rotating plate is rotated by the driving means around the driving axis. The bearing for the capsule housing body is mounted near the circumference part of the rotating plate, where an axis suppourted with this bearing is only rotatable in the reverse direction to the rotating direction of the rotating plate. The capsule housing body is fixed at the capsule housing body supporting axis, which is parallel to the driving axis of the driving means and supported with the bearing for the capsule housing body. The balance weight is fixed at the predetermined position of the rotating plate, and this position is approximately opposite to the capsule housing body beyond the driving axis of the driving means. The mechanism is for circularly moving the direction keeping axis in the same direction as the rotating direction of the rotating plate along a circle having the same diameter as but the different center from those of the circular movement of the capsule housing body supporting axis, and the direction keeping axis is parallel to the driving axis of the driving means and substantially fixed with the capsule housing body.

Further, it has been found out that the kneader for the tooth restoration material preferably comprises the following mechanisms. As for one constitution of mechanism for circularly moving the direction keeping axis in the same direction of the rotating plate along a circle having the same diameter as but the different center from those of the circular movement of the capsule body supporting axis, the direction keeping axis is fixed with a connection member having a length in a horizontal direction from the capsule housing body supporting axis, supported with a bearing for a guide groove which moves along the guide groove formed on a frame incorporated with the driving means, the center line of this groove is shaped in a circle having the same diameter as but the different center from those of the circular movement of the capsule housing body supporting axis. Further, as for another constitution of the mechanism for circularly moving the direction keeping axis in the same direction of the rotating plate along a circle having the same diameter but the different center from those of the circularly movement of the capsule body supporting axis, the direction keeping axis is directly fixed with the capsule housing body, and supported with the bearing for the guide groove which moves along the guide groove formed on a frame incorporated with the driving means, and a center line of this groove is shaped in a circle having the same diameter as but different center from those of the circular movement of the capsule body supporting axis. When the mechanism of the kneader for the tooth restoration material has the above constitutions, the direction keeping axis smoothly moves along the guide groove through the bearing for the guide groove. Thus, the capsule housing body can be circularly moved in the state of being exactly kept in the fixed direction without vibration or dislocation during the operation of the device, so that it is preferable. Further, the kneader for the tooth restoration material preferably comprises the following mechanisms, where an auxiliary rotating plate is used. As for one constitution of the mechanism for circularly moving the direction keeping axis in the same direction of the rotating plate along a circle having the same diameter as but the different center from those of the circular movement of the capsule body supporting axis, the direction keeping axis is directly fixed with the capsule housing body, one end of the auxiliary rotating plate center axis is supported with a rotating direction restriction bearing, the other end of this axis is fixed at an auxiliary rotating plate, the auxiliary rotating plate center axis is parallel to the driving axis of the driving means, the rotating direction restriction bearing is mounted at the frame incorporated with the driving means, and the axis supported with this bearing is rotatable only in the same direction of the rotating direction of the rotating plate. As for another constitution of the mechanism for circularly moving the direction keeping axis, one end of the auxiliary rotating plate center axis is supported with the rotating direction restriction bearing, the other end of this axis is fixed at the frame incorporated with the driving means, the auxiliary rotating plate center axis is parallel to the driving axis of the driving means, the rotating direction restriction bearing is mounted at the auxiliary rotating plate and is rotatable only in the same direction of the rotating direction of the rotating plate, the direction keeping axis is supported with a bearing for the auxiliary rotating plate mounted near the circumference part of the auxiliary rotating plate, and the bearing for the auxiliary rotating plate is mounted away from the auxiliary rotating plate center axis with the same distance as the distance between the driving axis of the driving means and the capsule housing body supporting axis. When the mechanism of the kneader for the tooth restoration material has the above constitutions, since the direction keeping axis is provided near the circumference part of the auxiliary rotating plate, which is rotated around the auxiliary rotating plate center axis, the direction keeping axis can be exactly circularly moved, so that it is preferable. Further, if the balance weight is fixed at the predetermined position of the auxiliary rotating plate approximately countering with the capsule housing body beyond the driving axis of the driving means, although the auxiliary rotating plate is easily inclined on a side of the capsule housing body since it is connected with the capsule housing body through the direction keeping axis, this plate can be rotated stably with the balance weight, so that it is preferable.

The kneader for the tooth restoration material according to the present invention is the kneader which circularly moves the capsule housing body housing and keeping the capsule for the tooth restoration material, with its longitudinal direction being kept in the fixed direction, in order to mix and knead the powder component and the liquid component of the tooth restoration material in the mixing compartment of the capsule for the tooth restoration material. Further, the kneader comprises the rotating plate, the bearing for the capsule housing body, the capsule housing body, the balance weight and the following mechanism. The rotating plate is rotated by the driving means around the driving axis. The bearing for the capsule housing body is mounted near the circumference part of the rotating plate, where the axis supported with this bearing is rotatable in the reverse direction to the rotating direction of the rotating plate. The capsule housing body is fixed at the capsule housing body supporting axis, which is parallel to the driving axis of the driving means and supported with the bearing for the capsule housing body. The balance weight is fixed at the predetermined position of the rotating plate, and this position is approximately opposite to the capsule housing body beyond the driving axis of the driving means. The mechanism is for circularly moving the direction axis in the same direction as the rotating direction of the rotating plate, where the circular movement of the direction keeping axis has the same diameter as but the different center from those of the circular movement of the capsule housing body supporting axis, and the direction keeping axis is parallel to the driving axis of the driving means and substantially fixed with the capsule housing body. This kneader for the tooth restoration material is different from the conventional kneader, where the capsule housing body is rotated with respect to the rotating plate by compulsorily rotating the capsule housing body supporting axis in the reverse direction to the rotating direction of the rotating plate with the same rotating angle as that of the rotating plate. The kneader for the tooth restoration material of the present invention comprises the mechanism, which circularly moves the direction keeping axis in the same direction as the rotating direction of the rotating plate, where the circular movement of the direction keeping axis has the same diameter as but the different center from those of the circularly movement of the capsule housing body supporting axis, and the direction keeping axis is parallel to the driving axis of the driving means for rotating the rotating plate and substantially fixed with the capsule housing body. Further, in this kneader, the capsule housing body supporting axis fixed with the capsule housing body is supported with the bearing for the capsule housing body, which is mounted near the circumference part, and the axis supported with this bearing is only rotatable in the reverse direction to the rotating direction of the rotating plate. Then, the capsule housing body housing the capsule for the tooth restoration material can be circularly moved in the state of being always kept in the fixed direction. Further, the kneader can have the high durability since no timing belt is used, and is hardly deteriorated even when chemicals adhere.

Further, if the kneader for the tooth restoration material preferably comprises the following mechanisms. As for one constitution of the mechanism for circularly moving the direction keeping axis in the same direction of the rotating plate along a circle having the same diameter as but the different center from those of the circularly movement of the capsule body supporting axis, the direction keeping axis is fixed with a connection member having a length in a horizontal direction from the capsule housing body supporting axis, and supported with a bearing for a guide groove which moves along the guide groove formed on a frame incorporated with the driving means, the center line of this groove is shaped in a circle having the same diameter as but the different center from those of the circularly movement of the capsule housing body supporting axis. Further, as for another constitution of the mechanism for circularly moving the direction keeping axis in the same direction of the rotating plate along a circle having the same diameter as but the different center from those of the circular movement of the capsule body supporting axis, the direction keeping axis is directly fixed with the capsule housing body, and supported with the bearing for the guide groove which moves along the guide groove formed on a frame incorporated with the driving means, and a center line of this groove is shaped in a circle having the same diameter as but different center from those of the circular movement of the capsule body supporting axis. When the mechanism of the kneader for the tooth restoration material has the above constitutions, the direction keeping axis smoothly moves along the guide groove through the bearing for the guide groove. Thus, the capsule housing body can be circularly moved in the state of being exactly kept in the fixed direction without vibration or dislocation during the operation of the device, so that it is preferable.

Further, the kneader for the tooth restoration material preferably comprises the following mechanisms, where the auxiliary rotating plate is used. As for one constitution of the mechanism for circularly moving the direction keeping axis in the same direction of the rotating plate along a circle having the same diameter as but the different center from those of the circular movement of the capsule body supporting axis, the direction keeping axis is directly fixed with the capsule housing body, one end of the auxiliary rotating plate center axis is supported with the rotating direction restriction bearing, the other end of this axis is fixed at an auxiliary rotating plate, the auxiliary rotating plate center axis is parallel to the driving axis of the driving means, the rotating direction restriction bearing is mounted at the frame incorporated with the driving means, and the axis supported with this bearing is rotatable only in the same direction of the rotating direction of the rotating plate. As for another constitution of the mechanism for circularly moving the direction keeping axis, one end of the auxiliary rotating plate center axis is supported with the rotating direction restriction bearing, and the other end of this axis is fixed at the frame incorporated with the driving means, the auxiliary rotating plate center axis is parallel to the driving axis of the driving means, the rotating direction restriction bearing is mounted at the auxiliary rotating plate and is rotatable only in the same direction of the rotating direction of the rotating plate, the direction keeping axis is supported with the bearing for the auxiliary rotating plate mounted near the circumference part of the auxiliary rotating plate, and the bearing for the auxiliary rotating plate is mounted away from the auxiliary rotating plate center axis with the same distance as the distance between the driving axis of the driving means and the capsule housing body supporting axis. When the mechanism of the kneader for the tooth restoration material has the above constitutions, since the direction keeping axis is provided near the circumference part of the auxiliary rotating plate, which is rotated around the auxiliary rotating plate center axis, the direction keeping axis can be circularly moved exactly, so that it is preferable.

Further, when the balance weight is fixed at the predetermined position of the auxiliary rotating plate approximately opposite to the capsule housing body beyond on the driving axis of the driving means, although the auxiliary rotating plate is easily inclined on a side of the capsule housing body since it is connected with the capsule housing body through the direction keeping axis, this plate can be rotated stably owing to the balance weight, so that it is preferable.

DETAILED DESCRIPTION OF PREFERRED EMBODIMENT

Hereinafter, the kneader for the tooth restoration material according to the present invention is explained concretely with drawings.

In the drawings, 1 is a capsule for a tooth restoration material, in which the powder component and the liquid component of the tooth restoration material are housed in a mixing compartment 1a. In the capsule 1 for the tooth restoration material, the fixed amounts of the powder component and the liquid component, which are weighted beforehand, are housed isolatedly, and used by breaking the partition or the like immediately before using thereof to mix and knead the two components.

2 is a driving means, which rotates a driving axis 2a and transmits a driving force. As the driving means 2, a general electric motor or the like can be used, and it is preferable that the driving means 2 comprises a controlling part for controlling rotation speed or operation time in order to mix and knead exactly.

Figure 2:
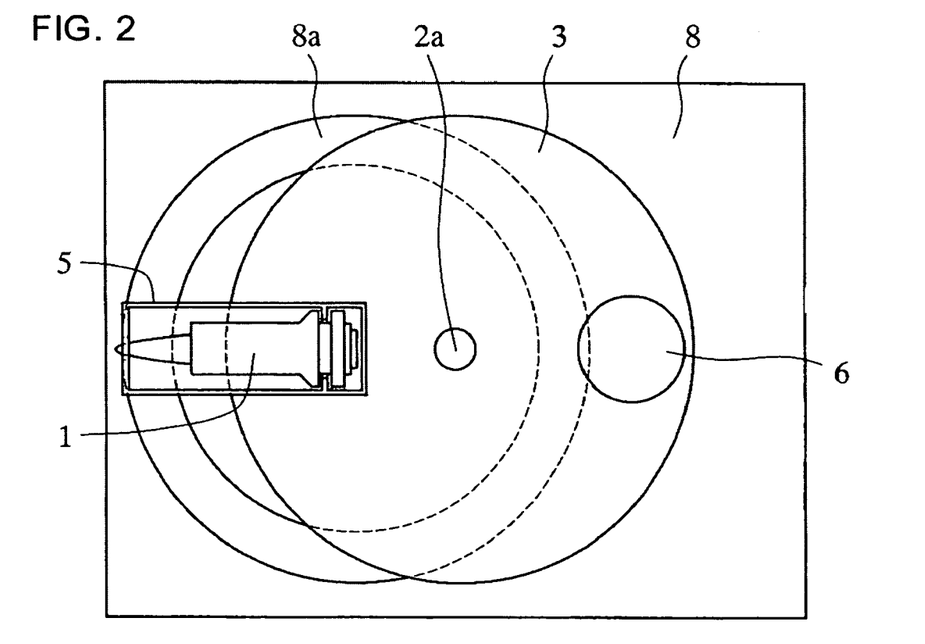
FIG. 2 is a plan explanation view of the kneader for the tooth restoration material in FIG. 1.

3 is a rotating plate, which is rotated by the driving means 2 around the driving axis 2a. As the rotating plate 3, plates having various shapes can be used, for example, a disk-like plate shown in FIG. 2, an approximate rectangular parallelepiped plate shown FIG. 7 or the like can be used.

4 is a bearing for a capsule housing body which is mounted near a circumference part of the rotating plate 3, and an axis supported with this bearing is rotatable only in a reverse direction to a rotating direction of the rotating plate 3. The bearing for the capsule housing body 4 is provided so as to rotate a capsule housing body supporting axis 5a mentioned below only in the reverse direction to the rotating direction of the rotating plate 3.

5 is a capsule housing body fixed with the capsule housing body supporting axis 5a, which is parallel to the driving axis 2a of the driving means 2 and supported with the bearing for the capsule housing body 4. In the capsule housing body 5, the capsule for the tooth restoration material 1 is housed and retained, and the capsule 1 is circularly moved in the state of its longitudinal direction being kept in the fixed direction.

6 is a balance weight, which is fixed at a predetermined position of the rotating plate 3 approximately countering opposite to with the capsule housing body 5 beyond the driving axis 2a of the driving means 2. The rotating plate 3 is easily inclined on a side of the capsule housing body 5 since the capsule housing body 5 is mounted at the rotating plate through the capsule housing body supporting axis 5a. So, the rotating plate 3 can be rotated stably by providing the balance weight 6. Further, when an auxiliary rotating plate 9 mentioned below is provided, the auxiliary rotating plate 9 is also easily inclined on the side of the capsule housing body 5 since it is connected with the capsule housing body 5 through a direction keeping axis 5b. So, when the balance weight 6 is similarly provided at the auxiliary rotating plate 9, the auxiliary rotating plate 9 can be rotated stably, so that it is preferable.

7 is a connection member having a length in a horizontal direction from the capsule housing body supporting axis 5a. Since the direction keeping axis 5b is fixed with the connection member 7, the capsule housing body supporting axis 5a and the direction keeping axis 5b are circularly moved in the state that they are linked each other. So, the circular movement and the rotating movement of the capsule housing body 5 can be certainly synchronized.

8 is a frame incorporated with the driving means 2. The frame 8 has a shape for rotatably mounting the driving axis 2a of the driving means 2 as shown in FIG. 1, or a shape for rotatably mounting an auxiliary rotating plate center axis 9a mentioned below of the auxiliary rotating plate 9 as shown in FIG. 6.

Figure 7:
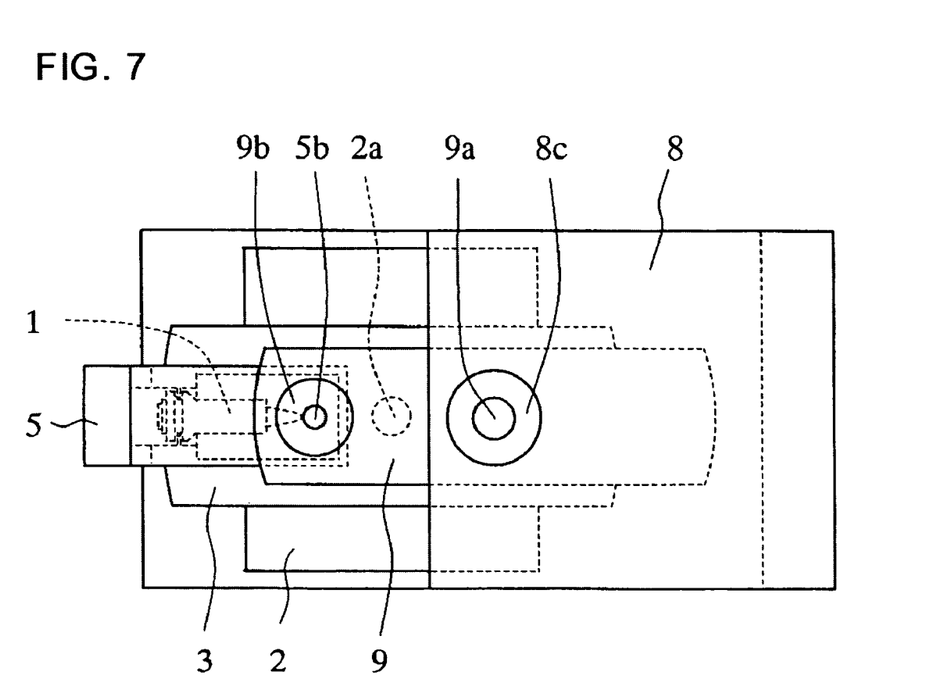
FIG. 7 is a plan explanation view of the kneader for the tooth restoration material in FIG. 6.

9 is an auxiliary rotating plate. As for the auxiliary rotating plate 9, when the direction keeping axis 5b is directly fixed with the capsule housing body 5, one constitution of the auxiliary rotating plate 9 is that a rotating direction restriction bearing 8c is mounted at the frame 8, one end of an auxiliary rotating plate center axis 9a is supported with this bearing, the other end of the auxiliary rotating plate center axis 9a is fixed at the auxiliary rotating plate 9, the rotating direction restriction bearing 8c can rotate an axis supported by it only in the same direction as the rotating direction of the rotating plate 3, the frame 8 is incorporated with the driving means 2, and the auxiliary rotating plate center axis 9a is parallel to the driving axis 2a of the driving means 2. The other constitution of the auxiliary rotating plate 9 is that the rotating direction restriction bearing 8c is mounted at the auxiliary rotating plate 9, one end of the auxiliary rotating plate center axis 9a is supported with this plate 9, the other end of the auxiliary rotating plate center axis 9a is fixed with the frame 8, the rotating direction restriction bearing 8c is rotatable only in the same direction as the rotating direction of the rotating plate 3, the frame 8 is incorporated with the driving means 2, and the auxiliary rotating plate center axis 9a is parallel to the driving axis 2a of the driving means 2. As the auxiliary rotating plate 9, although an approximate rectangular parallelepiped plate is shown in FIG. 7, various shapes including the disk shape like as in the case of the rotating plate 3, can be also used.

Figure 1:
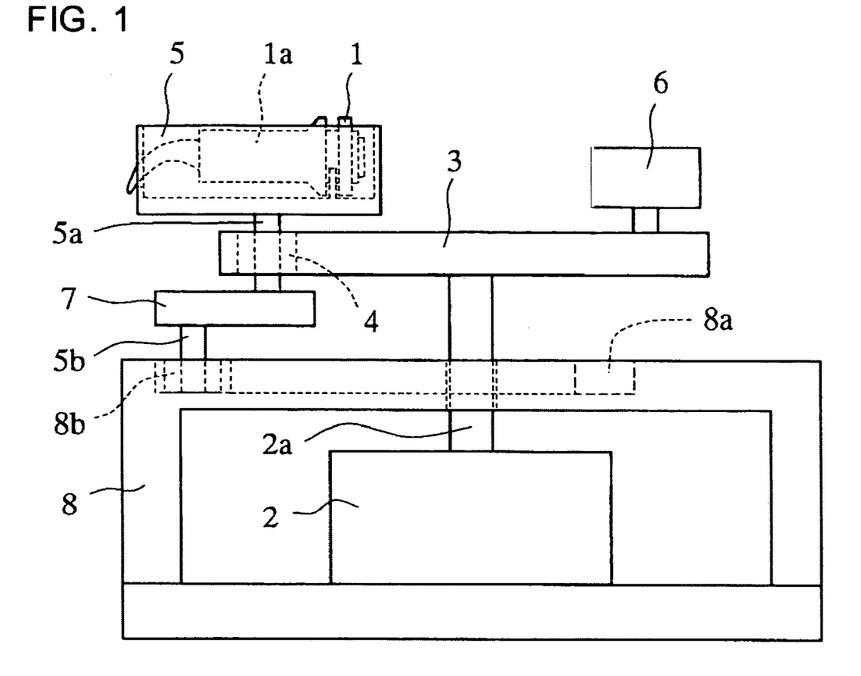
FIG. 1 is a front explanation view showing one example of the kneader for the tooth restoration material according to the present invention.
Figure 4:
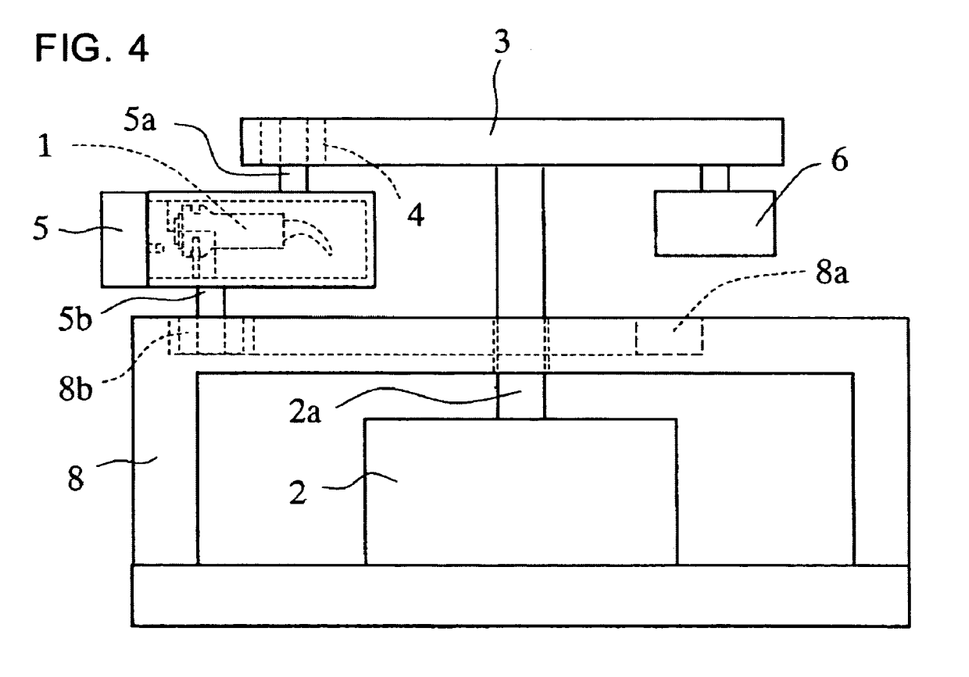
FIG. 4 is a front explanation view showing another example of the kneader for the tooth restoration material according to the present invention.
Figure 5:
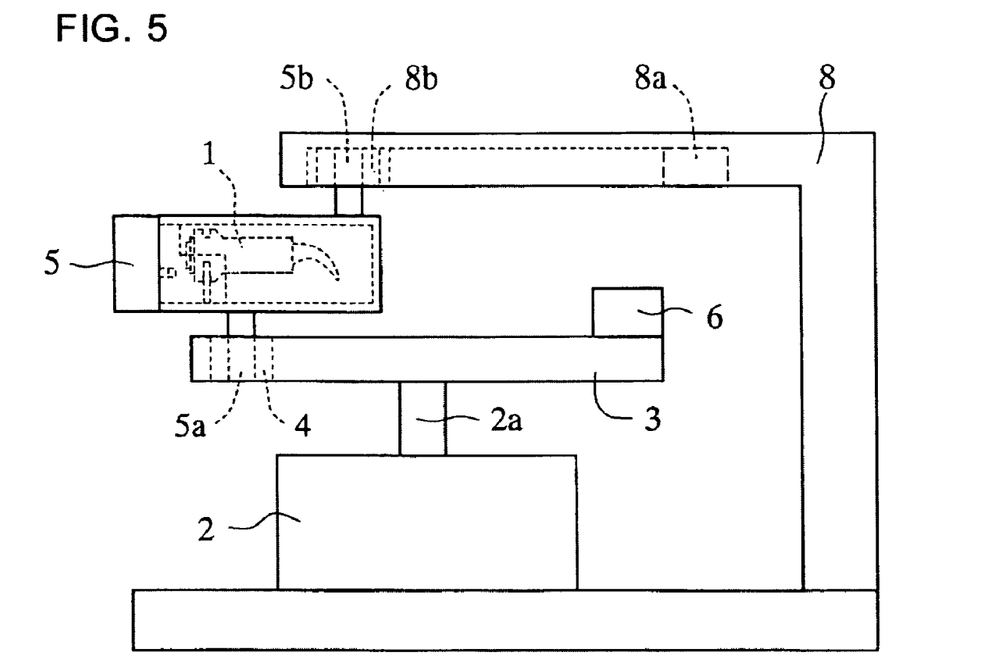
FIG. 5 is a front explanation view showing further another example of the kneader for the tooth restoration material according to the present invention.

Further, the kneader for the tooth restoration material comprises the mechanism for circularly moving the direction keeping axis 5b in the same direction of the rotating plate 3 along a circle having the same diameter as but the different center from those of the circular movement of the capsule body supporting axis 5a in which, as shown in FIG. 1, for example, the direction keeping axis 5b is fixed with a connection member 7 having a length in a horizontal direction from the capsule housing body supporting axis 5a, and supported with a bearing for a guide groove 8b which moves along the guide groove 8a formed on a frame 8 incorporated with the driving means 2, and the center line of the guide groove 8a is shaped in a circle having the same diameter as but the different center from those of the circular movement of the capsule housing body supporting axis 5a. Further, as shown in FIG. 4 and FIG. 5 for example, as another constitution of the mechanism for circularly moving the direction keeping axis 5b, the direction keeping axis 5b is directly fixed with the capsule housing body 5, and supported with the bearing for the guide groove 8b which moves along the guide groove 8a on the frame 8 incorporated with the driving means 2, and the center line of the guide groove 8a is shaped a circle having the same diameter as but the different center from those of the circularly movement of the capsule housing body supporting axis 5a. If the mechanism of the kneader for the tooth restoration material has the above constitutions, the direction keeping axis 5b smoothly moves along the guide groove 8a through the bearing for the guide groove 8b. Thus, the capsule housing body 5 can be circularly moved in the state of being exactly kept in the fixed direction without vibration or dislocation during the operation of the device.

Figure 6:
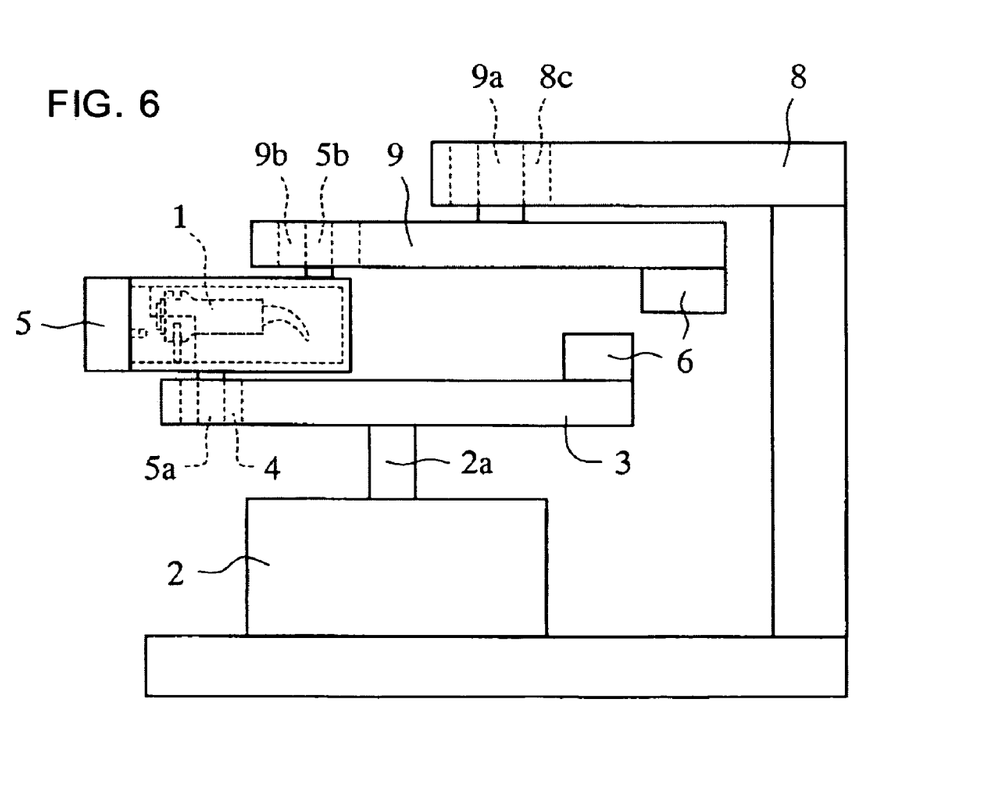
FIG. 6 is a front explanation view showing further another example of the kneader for the tooth restoration material according to the present invention.

Further, as shown in FIG. 6, the kneader for the tooth restoration material comprises the mechanism for circularly moving the direction keeping axis 5b in the same direction of the rotating plate 3 along a circle having the same diameter as but the different center from those of the circular movement of the capsule body supporting axis 5a, in which the direction keeping axis 5b is directly fixed with capsule housing body 5, one end of the auxiliary rotating plate center axis 9a is supported with a rotating direction restriction bearing 8c, the other end of this axis 9a is fixed at an auxiliary rotating plate 9, the auxiliary rotating plate center axis 9a is parallel to the driving axis 2a of the driving means 2, the rotating direction restriction bearing 8c is mounted at the frame 8 incorporated with the driving means 2, the axis supported with this bearing 8c is rotatable only in the same direction of the rotating direction of the rotating plate 3, the direction keeping axis 5b is supported with the bearing for the auxiliary rotating plate 9b, and the bearing for the auxiliary rotating plate 9b is mounted near the circumference part of the auxiliary rotating plate 9 and is away from the auxiliary rotating plate center axis 9a with the same distance as the distance between the driving axis 2a of the driving means 2 and the capsule housing body supporting axis 5a. When the mechanism has the above constitution, since the direction keeping axis 5b is provided near the circumference part of the auxiliary rotating plate 9, which is rotated around on the auxiliary rotating plate center axis 9a, the direction keeping axis 5b can be circularly moved exactly.

Further, as another constitution of the mechanism for circularly moving the direction keeping axis 5b in the same direction of the rotating plate 3 along a circle having the same diameter as but the different center from those of the circular movement of the capsule body supporting axis 5a, which is not shown in figure, the direction keeping axis 5b is directly fixed with capsule housing body 5, one end of the auxiliary rotating plate center axis 9a is supported with the rotating direction restriction bearing 8c, the other end of this axis 9a is fixed at the frame 8 incorporated with the driving means 2, the frame 8 is parallel to the driving axis 2a of the driving mean 2, the rotating direction restriction bearing 8c is mounted at the auxiliary rotating plate 9 and is rotatable only in the same direction of the rotating direction of the rotating plate 3, the direction keeping axis 5b is supported with the bearing for the auxiliary rotating plate 9b, and bearing for the auxiliary rotating plate 9b is mounted near the circumference part of the auxiliary rotating plate 9 and is away from the auxiliary rotating plate center axis 9a with the same distance as the distance between the driving axis 2a of the driving means 2 and the capsule housing body supporting axis 5a. When the mechanism of the kneader for the tooth restoration material has the above constitutions, since the direction keeping axis 5b is provided near the circumference part of the auxiliary rotating plate, which is rotated around the auxiliary rotating plate center axis 9a, the direction keeping axis 5b can be circularly moved exactly, so that it is preferable.

Figure 3:
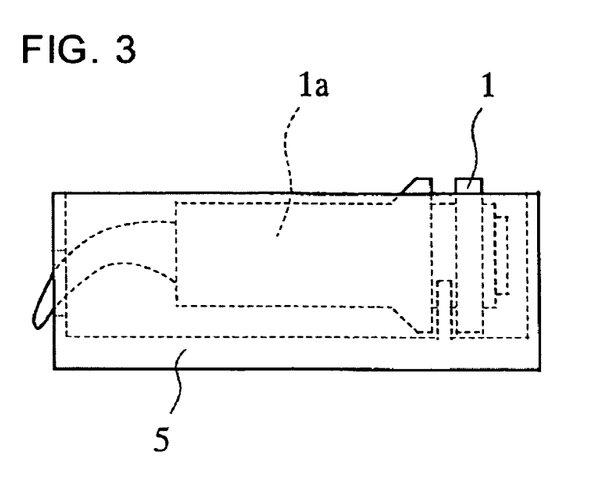
FIG. 3 is an enlarged front explanation view showing the capsule housing body in FIG. 1.

Further, in order to actually use the kneader for the tooth restoration material according to the present invention shown in FIG. 1, a top end part of the capsule 1 for the tooth restoration material is inserted into a through hole of the capsule housing body 5 and housed in the capsule housing body 5 so as to place it from an upper side at first, as shown in FIG. 3, where the capsule 1 is made in the state that the two components being the powder component and the liquid component for the tooth restoration material can be readily mixed and kneaded by breaking the partition or the like. Then, the driving means 2 is started to rotate the rotating plate 3 fixed with the driving axis 2a. The bearing for the capsule housing body 4 is mounted near the circumference part of the rotating plate 3, and an axis supported with this bearing for the capsule housing body 4 is rotatable only in the reverse direction to the rotating direction of the rotating plate 3. Further, the capsule housing body supporting axis 5a, which is parallel to the driving axis 2a of the driving means 2, is supported with the bearing for the capsule housing body 4. The capsule housing body 5 is fixed at a top end of the capsule housing body supporting axis 5a. Thus, when the rotating plate 3 is rotated, the capsule housing body 5 positioned near the circumference part of the rotating palate 3 is circularly moved around the driving axis 2a of the driving means 2. Further, the rotating plate 3 is easily inclined on the side of the capsule housing body 5 since it is connected with the capsule housing body 5 through the capsule housing body supporting axis 5a, therefore the balance weight 6 is provided in order to stably rotate the rotating palate 3. Further, when the balance weight 6 is provided so as to locate the center of gravity on the approximately same height as that of the gravity of the capsule housing body 5 as shown in FIG. 1, the rotation of the rotating palate 3 becomes further stable, so that it is preferable.

Then, since the direction keeping axis 5b is connected with the capsule housing body supporting axis 5a with the connection member 7 having the length in the horizontal direction, the direction keeping axis 5b is moved linking with the capsule housing body supporting axis 5a, where the capsule housing body supporting 5a is circularly moved together with the rotating plate 3. Further, since the direction keeping axis 5b moves along the guide groove 8a through the bearing for the guide groove 8b, the direction keeping axis 5b is circularly moved in the same direction as that of the capsule housing body supporting axis 5a, i.e., the rotating direction of the rotating plate 3. Further, since the guide groove 8a is formed so that the center line of the guide groove 8a is shaped in a circle having the same diameter as but the different center from those of the circular movement of the capsule housing body supporting axis 5a, the direction keeping axis 5b is circularly moved along a circle having the same diameter as but the different center from those of the circular movement of the capsule housing body supporting axis 5a.

In this way, the capsule housing body supporting axis 5a fixed with the capsule housing body 5 and the direction keeping axis 5b substantially fixed with the capsule housing body 5 are circularly moved along circles having the same diameters as but the different centers respectively in the same direction, i.e., the rotating direction of the rotating plate 3. Then, when the capsule housing body 5 is circularly moved at a certain angle around the driving axis 2a of the driving means 2, the capsule housing body itself is rotated only at the same angle as that of the circular movement. Thus, the capsule housing body 5 housing the capsule 1 for the tooth restoration material can be circularly moved in the state of being always kept in the fixed direction. Further, since the timing belt or the like is not used, the durability is high, and it is hardly deteriorated even if chemicals adhere.

Figure 8:
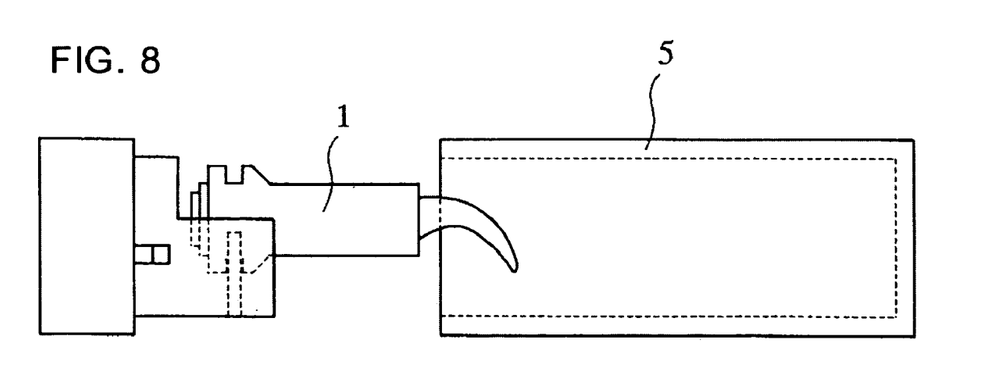
FIG. 8 is an enlarged front explanation view showing a structure of the capsule housing body in FIG. 4 to FIG. 6.

Further, when the kneader for the tooth restoration material according to the present invention shown in FIGS. 4 and 5 is used, the capsule 1 for the tooth restoration material is housed in a dividable capsule housing body 5 shown in FIG. 8 at first, wherein the capsule 1 is in the state that the two components being the powder component and the liquid component for the tooth restoration material can be readily mixed and kneaded by breaking the partition or the like. Then, the driving means 2 is started to rotate the rotating plate 3 fixed at the driving axis 2*a*. Near the circumference part of the rotating plate 3, the bearing for the capsule housing body 4 is mounted, like the kneader for the tooth restoration material according to the present invention shown in FIG. 1. The axis supported with this bearing for the capsule housing body 4 is rotatable only in the reverse direction to the rotating direction of the rotating plate 3. Further, the capsule housing body supporting axis 5*a*, which is parallel to the driving axis 2*a* of the driving means 2, is supported with the bearing for the capsule housing body 4, and the capsule housing body 5 is fixed at the top end of the capsule housing body supporting axis 5*a*. Thus, when the rotating plate 3 is rotated, the capsule housing body 5 positioned near the circumference part of the rotating plate 3 is circularly moved around the driving axis 2*a* of the driving means 2. Further, since the direction keeping axis 5*b* is connected with the capsule housing body supporting axis 5*a* by the capsule housing body 5, the direction keeping axis 5*b* is moved linking with the capsule housing body supporting axis 5*a*, where the capsule housing body supporting axis 5*a* is circularly moved together with the rotating palate 3. Since the direction keeping axis 5*b* moves along the guide groove 8*a* through the bearing for the guide groove 8*b*, the direction keeping axis 5*b* is circularly moved in the same direction as that of the capsule housing body supporting axis 5*a*, i.e., the rotating direction of the rotating plate 3. Further, the guide groove 8*a* is formed so that the center line of the guide groove 8*a* is shaped in a circle having the same diameter as but the different center from those of the circular movement of the capsule housing body supporting axis 5*a*. Thus, the direction keeping axis 5*b* is circularly moved along a circle having the same diameter as but the different center from those of the circularly movement of the capsule housing body supporting axis 5*a*.

Further, when the kneader for the tooth restoration material according to the present invention shown in FIG. 6 is used, the capsule 1 for the tooth restoration material is housed in the dividable capsule housing body 5 shown in FIG. 8 at first, where the capsule 1 is made in the state that the two components, i.e., the powder component and the liquid component for the tooth restoration material, can be readily mixed and kneaded by breaking the partition or the like. Then, the driving means 2 is started to rotate the rotating plate 3 fixed with the driving axis 2*a*. Near the circumference part of the rotating plate 3, the bearing for the capsule housing body 4 is mounted, where the axis supported with this bearing 4 is rotatable only in the reverse direction to the rotating direction of the rotating plate 3. Further, the capsule housing body supporting axis 5*a*, which is parallel to the driving axis 2*a* of the driving means 2, is supported with the bearing for the capsule housing body 4. The capsule housing body 5 is fixed with the top end of the capsule housing body supporting axis 5*a*. Thus, when the rotating plate 3 is rotated, the capsule housing body 5 positioned near the circumference part of the rotating plate 3 is circularly moved around the driving axis 2*a* of the driving means 2.

Further, the auxiliary rotating plate center axis 9*a* is mounted at the frame 8 in parallel with the driving axis 2*a* of the driving means 2 and the auxiliary rotating plate 9 is fixed with the auxiliary rotating plate center axis 9*a*. The auxiliary rotating plate center axis 9*a* is supported with the rotating direction restriction bearing 8*c*, which is mounted at the frame 8 or the auxiliary rotating plate 9. The rotating direction restriction bearing 8*c* is rotatable only in the same direction as the rotating direction of the rotating plate 3. Thus, the direction keeping axis 5*b* is circularly moved around the auxiliary rotating plate center axis 9*a* in the same direction as that of the capsule housing body supporting axis 5*a*, i.e., the rotating direction of the rotating plate 3. Further, since the distance between the driving axis 2*a* of the driving means 2 and the capsule housing body supporting axis 5*a* is same as the distance between the auxiliary rotating plate center axis 9*a* and the direction keeping axis 5*b*, the direction keeping axis 5*b* is circularly moved along a circle having the same diameter as that of the capsule housing body supporting axis 5*a*. In addition, the auxiliary rotating plate 9 is easily inclined on the side of the capsule housing body 5 since it is connected with the capsule housing body 5 through the direction keeping axis 5*b*, therefore it is preferable that the balance weight 6 is provided. Further, it is preferable that the balance weight 6 fixed at the auxiliary rotating plate 9 is fixed considering the position of the balance weight 6 fixed at the rotating plate 3. For example, as shown in FIG. 6, when the centers of gravity of the two balance weights 6 fixed at the auxiliary rotating plate 9 and the rotating plate 3 is positioned at the approximately same heights as that of the capsule housing body 5, the vibration or the like is hardly generated to the whole of the device, so that it is more preferable.

The capsule housing body supporting axis 5*a* fixed with the capsule housing body 5 and the direction keeping axis 5*b* connected with the capsule housing body 5 are circularly moved around circles having the same diameters but the different centers respectively in the same direction, i.e., the rotating direction of the rotating plate 3, respectively in this way. Thus, when the capsule housing body 5 is circularly moved at the certain angle around the driving axis 2*a* of the driving means 2, the capsule housing body 5 itself is rotated at the same angle as that of the circular movement. Then, the capsule housing body 5 housing the capsule 1 can be circularly moved in the state of being always kept in the fixed direction.

What is claimed is:

1. A kneader for a tooth restoration material, which circularly moves a capsule housing body housing and keeping a capsule for a tooth restoration material with its longitudinal direction being kept in a fixed direction, in order to mix and knead a powder component and a liquid component of the tooth restoration material in a mixing compartment of the capsule for the tooth restoration material, comprising, a rotating plate rotated in a rotating direction around a driving axis by a driving means a bearing for a capsule housing body mounted near a circumference part of said rotating plate, an axis supported with said bearing for a capsule housing body being rotatable only in a reverse direction to the rotating direction of said rotating plate, a capsule housing body fixed with a capsule housing body supporting axis, which is parallel to the driving axis of said driving means and supported with said bearing for the capsule housing body, a balance weight fixed at a predetermined position of said rotating plate approximately opposite to said capsule housing body beyond the driving axis of said driving means, and a mechanism for circularly moving a direction keeping axis for keeping the direction of a capsule housing body in a same direction as the rotating direction of said rotating plate, along a circle having a same diameter as but the different center from those of the circular movement of the capsule housing body supporting axis, the direction keeping axis being parallel to the driving axis of said driving means, and substantially fixed with the capsule housing body.

2. The kneader for the tooth restoration material claimed in claim 1, wherein the mechanism for circularly moving the direction keeping axis in the same direction as the rotating direction of the rotating plate along the circle having the same diameter as but the different center from those of the circular movement of the capsule housing body supporting axis, is structure such that the direction keeping axis is fixed with a connection member having a length in a horizontal direction from the capsule housing body supporting axis and supported with a bearing for a guide groove moving along a guide groove, which is formed on a frame incorporated with the driving means, and a center line of the guide groove is shaped in a circle having the same diameter as but the different center from those of the circular movement of the capsule housing body supporting axis.

3. The kneader for the tooth restoration material claimed in claim 1, wherein the mechanism for circularly moving the direction keeping axis in the same direction as the rotating direction of the rotating plate along a circle having the same diameter as but the different center from those of the circularly movement of the capsule housing body supporting axis, is structured such that the direction keeping axis is directly fixed with the capsule housing body and supported with the bearing for the guide groove moving along the guide groove, which is formed on the frame incorporated with the driving means, and the center line of said guide groove is shaped in the circle having the same diameter as but the different center from those of the circular movement of the capsule housing body supporting axis.

4. The kneader for the tooth restoration material claimed in claim 1, wherein the mechanism for circularly moving the direction keeping axis in the same direction as the rotating direction of the rotating plate along each circle having the same diameter as but the different center from those of the circularly movement of the capsule housing body supporting axis, is structure such that the direction keeping axis is directly fixed with the capsule housing body, one end of an auxiliary rotating plate center axis is supported with a rotating direction restriction bearing, the other end of an auxiliary rotating plate center axis is fixed with an auxiliary rotating plate, said auxiliary rotating plate center axis is parallel to the driving axis of said driving means, the rotating direction restriction bearing is mounted at the frame incorporated with the driving means, and the axis supported with the rotating direction restriction bearing is rotatable only in the same direction of the rotating direction of the rotating plate, or one end of the auxiliary rotating plate center axis is supported with the rotating direction restriction bearing, the other end of the auxiliary rotating plate center axis is fixed at the frame incorporated with the driving means, the auxiliary rotating plate center axis is parallel to the driving axis of the driving means, the rotating direction restriction bearing is mounted at the auxiliary rotating plate and is rotatable only in the same direction of the rotating direction of the rotating plate and the direction keeping axis is supported with a bearing for the auxiliary rotating plate, which is mounted near the circumference part of the auxiliary rotating plate, and the bearing for the auxiliary rotating plate is mounted away from the auxiliary rotating plate center axis with a same distance as a distance between the driving axis of said driving means and the capsule housing body supporting axis.

5. The kneader for the tooth restoration material claimed in claim 4, wherein the balance weight is fixed at the predetermined position of the auxiliary rotating plate approximately opposite to the capsule housing body beyond the driving axis of the driving means.

* * * * *